(12) United States Patent
Gayed

(10) Patent No.: US 7,432,360 B2
(45) Date of Patent: *Oct. 7, 2008

(54) MULTI-DOSE ERYTHROPOIETIN FORMULATIONS

(75) Inventor: Atef Gayed, Overland Park, KS (US)

(73) Assignee: Aventis Pharmaceuticals Inc., Bridgewater, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/167,818

(22) Filed: Jun. 27, 2005

(65) Prior Publication Data

US 2005/0267033 A1   Dec. 1, 2005

(51) Int. Cl.
*C07K 14/00* (2006.01)
(52) U.S. Cl. .................................. 530/388.23
(58) Field of Classification Search ............. 530/388.23
See application file for complete search history.

(56) References Cited

U.S. PATENT DOCUMENTS

| | | | | |
|---|---|---|---|---|
| 3,489,837 | A | * 1/1970 | Hyman | ........................ 514/297 |
| 4,377,513 | A | 3/1983 | Sugimoto et al. | |
| 4,703,008 | A | 10/1987 | Lin | |
| 4,806,524 | A | 2/1989 | Kawaguchi et al. | |
| 4,879,272 | A | * 11/1989 | Shimoda et al. | ................ 514/8 |
| 5,045,529 | A | 9/1991 | Chiang | ........................... 514/6 |
| 5,503,827 | A | 4/1996 | Woog et al. | ................ 424/85.1 |
| 5,554,378 | A | * 9/1996 | Uda et al. | .................... 424/434 |
| 5,661,125 | A | 8/1997 | Strickland et al. | |

FOREIGN PATENT DOCUMENTS

| | | | | |
|---|---|---|---|---|
| EP | 0 199 992 | 11/1986 | ...................... 37/2 |
| EP | 0 459 795 | 5/1991 | ...................... 37/2 |

OTHER PUBLICATIONS

Sandeep et al. Excipients and their use in injectable products (1997) PDA J. Pharm. Sci Technol. vol. 51, No. 4, pp. 166-171.*
Durieux, Marcel E., M.D., "Synergistic Inhibition of Muscarinic Signaling by Ketamine Stereoisomers and the Preservative Benzethonium Chloride," *Anesthesiology* 86:1326-33 (1997).
Miyake, et al., "Purification of Human Erythropoietin," *J. Biol. Chem.*, 252(15):5558-64 (1977).
Sherwood, et al., "Erythropoietin Production by Human Renal Carcinoma Cells in Culture," *Endocrinology*, 99(2):504-10 (1976).
Sherwood, et al., "Establishment of a Human Erythropoietin-Producing Renal Carcinoma Cell Line," *Clinical Research*, 31:323A (1983).
Lee, Minhwa and Gu, Youngsoon, Ewha; New Pharmaceuticals; Women's University Publishing; p. 221 (1989).
Pivnick, H. et al.; "Preservatives for Poliomyelitis (Salk) Vaccine III 2-Phenoxyethanol," *J. Pharmaceutical Sciences*; 53(8); 899-901 (1964).

* cited by examiner

*Primary Examiner*—Karen Cochrane Carlson
(74) *Attorney, Agent, or Firm*—Vinson & Elkins LLP

(57) ABSTRACT

The present invention is directed to multi-dose erythropoietin formulations for parenteral administrations. The formulations contain one or more of the following preservatives benzethonium chloride, phenoxyethanol and phenylethyl alcohol.

39 Claims, No Drawings

MULTI-DOSE ERYTHROPOIETIN FORMULATIONS

BACKGROUND OF THE INVENTION

I. Field of the Invention

The present invention pertains to multi-dose formulations of erythropoietin (hereinafter "EPO"), comprising a particularly advantageous preservative or combination of preservatives. Specifically, the present invention pertains to the use of the preservatives benzethonium chloride, phenoxyethanol and phenylethyl alcohol, alone or in combination, in multi-dose EPO formulations. The invention disclosed herein also relates to a method of treating a patient with an EPO-containing composition comprising benzethonium chloride, phenoxyethanol and/or phenylethyl alcohol. The present invention further relates to a pharmaceutical carrier composition; a vial for containing a composition; and a method of inhibiting microbial growth in a solution; wherein all compositions or solutions comprise EPO and one or more of the preservatives benzethonium chloride, phenoxyethanol and phenylethyl alcohol.

II. Background of the Invention

Sterility is one of the most important characteristics of parenteral products. For parenteral products that are sterilized and intended for single dose injection, maintenance of sterility is a function of both the method of sterilization and the integrity of the packaging system. For parenteral products that are intended for multiple dosing, antimicrobial agents must be added to the product formulation to protect the product from accidental microbial contamination during its storage and/or use.

Stable protein-containing multi-dose pharmaceutical formulations are viewed by the pharmaceutical industry as particularly advantageous and commercially attractive. Multi-dose formulations are generally, though not always, contained in vials (multi-dose containers) that allow for the extraction of partial amounts of the formulation at various times. This type of system is desirable as it allows multiple doses to be obtained from a single container, and allows for more controlled administration of the pharmaceutical composition as the formulation may be withdrawn and administered in any partial amount.

The nature of the use of multi-dose formulations imposes special requirements on the formulation. For example, maintenance of the sterility of the composition is particularly challenging given the many opportunities for introduction of microorganisms and other contaminants into the formulations. Repeated introduction of foreign elements, for example, needles, into the multi-dose container after formulation creates a likelihood of introducing microorganisms into the container. Additionally and alternatively, microorganisms may be introduced during filling of the containers, or during reconstitution of the formulations after lyophilization and prior to administration. The extended periods of time over which the container may be stored—especially during multiple introductions of foreign elements, and/or after contaminants may have been introduced, demands that the formulation contain special additives to insure the sterility of the contents.

To insure that multi-dose formulations maintain optimally sterile properties, the United States Food and Drug Administration (FDA) and regulatory agencies in other jurisdictions require that all multi-dose formulations contain preservatives to prevent the growth of, or to affirmatively kill, any microorganisms that may be introduced into the formulations. Given the inherent instability of proteins, and their tendency to interact adversely with preservative compounds, the development of protein containing multi-dose formulations has proven particularly difficult. Possible adverse interactions between preservatives and proteins include the degradation of the protein, especially when stored for extended periods of time; inactivation of the protein; formation of protein aggregates; and other interactions that inactivate the formulation or make administration of the formulation to humans, particularly by infusion, injection or other parenteral administration, difficult, painful or otherwise undesirable.

Additionally, preservatives themselves are noted for causing acute adverse reactions, such as allergic reactions, in humans upon parenteral administration. Ideally, the preservative contained in the multi-dose protein pharmaceutical composition should be effective in low concentration against a wide variety of micro organisms, soluble in the formulation, non-toxic, compatible and non-reactive with the protein, active with long term stability, and non-reactive with components of the container or closure system.

Sandeep Nema et al. published lists of various excipients that have been included in the formulation of injectable products marketed in the USA. The antimicrobial preservatives listed in this review article are included in Table 1:

TABLE 1

ANTIMICROBIAL PRESERVATIVES

| Preservative | Frequency | Range |
| --- | --- | --- |
| Benzalkonium chloride | 1 | 0.02% w/v |
| Benzethonium chloride | 4 | 0.01% |
| Benzyl alcohol | 74 | 0.75-5% |
| Chlorobutanol | 17 | 0.25-0.5% |
| m-cresol | 3 | 0.1-0.3% |
| Myristyl gamma-picolinium chloride | 2 | 0.0195-0.169% |
| Paraben methyl | 50 | 0.05-0.18% |
| Paraben propyl | 40 | 0.01-0.1% |
| Phenol | 48 | 0.2-0.5% |
| 2-Phenoxyethanol | 3 | 0.50% |
| Phenyl mercuric nitrate | 3 | 0.001% |
| Thimerosal | 46 | 0.003-0.01% |

EPO is a glycoprotein that functions to stimulate the production of hemoglobin and erythrocytes in bone marrow. It is produced in the kidney, and is widely used as a treatment for anemia caused by a variety of conditions, including, for example, renal failure. The amino acid sequence and general glycosylation patterns of EPO are known in the art. See, for example, Miyaka et al. and U.S. Pat. No. 4,703,008. Isolation and Purification of EPO, from human tissues or fluids, has been described by Miyake et al.

The nucleic acid sequence encoding the protein, isolation of this sequence, and production of the protein by traditional recombination methods are also known in the art. See, for example, U.S. Pat. No. 4,703,008 to Lin, describing the nucleic acid sequence encoding EPO; U.S. Pat. No. 4,337,513 to Sugimoto et al., describing the use of lymphoblastoid cells to produce EPO; and Sherwood et al., describing production of EPO by a human renal carcinoma cell line. Additionally, production, isolation and purification of the protein is also achievable by gene-activation, or homologous recombination, followed by well-known isolation and purification techniques.

Development of EPO-containing multi-dose formulations has proven particularly difficult by virtue of the particular instability displayed by EPO, and its tendency to readily interact with common pharmaceutical ingredients. U.S. Pat. No. 4,806,524. Attempts to develop multi-dose EPO formulations have tried to circumvent these problems by maintaining the formulations at a low pH, or by including various amino acid constructs, two approaches thought to assist in the stabilization of the EPO protein, or by developing lyophilized forms in which the preservative sublimes from the formulation before administration. U.S. Pat. No. 5,503,827 (the '827 patent) to Woog.

Stable, sterile multi-dose EPO-containing pharmaceutical formulations are few. They include those formulations disclosed in the '827 patent. The '827 reference discloses and specifically claims chloretone (chlorbutanol, 1,1,1-trichloro-2-methyl-2-propanol), benzalkonium chloride or benzyl alcohol as preservatives. Woog specifically notes the particular difficulty of providing a multi-dose EPO formulation in which the allergy rates are reduced, and promotes the use of the specifically claimed preservatives as especially advantageous in that regard. This reference further stresses that due to the tendency of preservatives to degrade and proteins to be inactivated when combined, it is most desirable to minimize contact between the preservative and the protein. The '827 patent further discloses the use of several amino acid constructs and other additives thought necessary to stabilize EPO in solution. Finally, The '827 patent discloses, in a most preferred embodiment that any preservative used in the initial formulation is sublimed away upon lyophilization of the composition. Then, upon reconstitution, additional preservative selected from the group disclosed (chloretone) as defined, benzalkonium chloride and benzyl alcohol, may be introduced, but the injectable, reconstituted solution should be used within 30 days.

Another example of an EPO-containing multi-dose formulation is described in U.S. Pat. No. 5,661,125 (the '125 patent). This patent explicitly acknowledges and affirms other references stating that EPO "is an instable substance especially in solution form" and "when combined with known stabilizers, the resulting stability of the EPO is varied and unpredictable." This reference then goes on to show and claim the specific use of benzyl alcohol, a paraben and/or a phenol or a combination of these as a preservative in EPO-containing solutions. Further attesting to the difficulty of discerning compatible and advantageous preservatives for use in EPO-containing multi-dose formulations, this reference states:

" . . . nothing specific can be derived from the use of preservatives with other proteins that would suggest any particular preserved formulation for erythropoietin. See, e.g., Geigert, J., 'Overview of the Stability and Handling of Recombinant Protein Drugs,' *Journal of Parenteral Science & Technology*, Vol. 43(5):220-224 (1989)".

Accordingly, there remains a need for an EPO-containing, preserved, multi-dose pharmaceutical formulation that: (1) maintains the stability of the protein component and the composition over an extended shelf life of the product; (2) maintains the sterility of the formulation and meets the United States, European and Japanese Pharmacopia criteria for preservative challenge testing; (3) is safe in the concentrations used; and (4) is administrable—by any parenteral or oral route—in a manner that is effective, and minimizes pain and the chance of adverse reaction, for example, allergic reaction, in the patient.

SUMMARY OF THE INVENTION

The present invention provides a novel and particularly advantageous multi-dose formulation containing erythropoietin and the preservatives benzethonium chloride, phenoxyethanol and phenylethyl alcohol, either alone or in combination.

The formulations of the present invention may be formulated in a variety of concentrations in various vial sizes for various administration dosages. For example, the formulations disclosed in the present invention may comprise 10,000, 20,000, 40,000, or even up to or greater than 100,000 Unit/ml EPO concentrations. They may further contain any concentrations in between these exemplary concentrations, such as 5,000, 15,000, 25,000 unit/ml concentrations, and the like. Additionally, the dosages may be formulated in a ½, 1 or 2 ml vial, or any other size vial or other container preferred by the formulator. It will be clear to one of skill in the art, that any combination of dosages and vials may be used, depending upon the needs of the formulator. For example, one could prepare the presently disclosed formulations as a 10,000 unit/ ½ ml concentration in a 1 ml vial, a 40,000 unit/ml dose in a 2 ml vial, or any other combination of concentration of EPO in any size vial. The compositions may be in the form of an aqueous solution, a suspension, or may be lyophilized.

The present invention provides in an alternative embodiment, a pharmaceutical carrier composition, for use as a carrier of EPO, comprising the preservatives benzethonium chloride, phenoxyethanol, or phenylethyl alcohol, wherein the preservatives are contained in the EPO carrier composition alone or in combination. The present invention also provides a vial for containing multiple doses of EPO, wherein the vial comprises EPO and an effective amount of one or a combination of the following preservatives: benzethonium chloride, phenoxyethanol, and phenylethyl alcohol.

In yet another embodiment, the present invention provides a method inhibiting microbial growth in an EPO-containing solution, wherein the method comprises adding to the EPO-containing solution, one or a combination of the following preservatives: benzethonium chloride, phenoxyethanol, and phenylethyl alcohol.

Additional components of the EPO multi-dose formulations of the present invention include surfactants, buffers, osmolality adjusting agents and antiadsorbants. Particularly advantageous additives include polysorbate-20, polysorbate-80, sodium phosphate, sodium chloride and genapol.

The formulations of the present invention may be in solid, semi-solid, liquid or fluid form, for example, as tablet, aqueous solution or a suspension, or may be lyophilized and reconstituted prior to administration to a patient. The formulations may be administered via any parenteral route, including intravenous, subcutaneous, intramuscular, transdermal, intra-arterial, intra-peritoneal, or via pulmonary inhalation. They may also be administered orally.

DETAILED DESCRIPTION OF THE INVENTION

The present invention provides a significant improvement over the state of the art. Provided are novel EPO-containing multi-dose pharmaceutical formulations containing preservatives that individually provide for stable, sterile, easily administered compositions. Further, and most unexpectedly, the present invention discloses that phenoxyethanol and benzethonium chloride, when used in combination in an EPO-containing multi-dose pharmaceutical composition, have positive synergistic effects resulting in a particularly advantageous composition. Specifically, this combination of preservatives displays the following characteristics: (1) synergistic antimicrobial effect, allowing for a lower concentration of preservatives to be used; (2) excellent stability of the EPO, at varying storage conditions, over extended periods of time; and (3) phenoxyethanol has a potential for a local anesthetic effect, making the composition particularly preferable for subcutaneous administration.

As used herein, the following terms have the following meanings:

Erythropoietin—a glycoprotein which, when in biologically active and glycosylated form, has the capacity to induce the formation of hemoglobin and red blood cells in bone marrow. May be obtained via isolation from human tissues or fluids, by traditional recombination methods, or by gene activation.

Parenteral—by some means other than the gastrointestinal tract; includes intravenous, subcutaneous, intramuscular, and intramedullary, intra-arterial, intra-peritoneal and pulmonary inhalation.

Pharmaceutically acceptable (or pharmacologically acceptable)—refers to molecular entities and compositions that do not produce an adverse, allergic or other untoward reaction when administered to an animal or a human, as appropriate.

Pharmaceutically acceptable carrier—includes any and all solvents, dispersion media, coatings, antibacterial and antifungal agents, isotonic and absorption delaying agents and the like, that may be used as a media for a pharmaceutically acceptable substance.

Unit—a unit of biological activity as determined by exhypoxic polyeythemic mouse bioassay and compared to World Health Organization standards.

Any numerical values recited herein include all values from the lower value to the upper value in increments of one unit provided that there is a separation of at least 2 units between any lower value and any higher value. As an example, if it is stated that the concentration of a component or a value of a process variable such as, for example, osmolality, temperature, pressure, time and the like is, for example, from 1 to 90, preferably from 20 to 80, more preferably from 30 to 70, it is intended that values such as 15 to 85, 22 to 68, 43 to 51, 30 to 32 etc. are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner.

A. Preservatives: Phenoxyethanol and Benzethonium Chloride

The preservatives contemplated for use according to the present invention are preferably benzethonium chloride, phenoxyethanol and phenylethyl alcohol, any variants of these preservatives and their structural analogues. It is specifically contemplated that any of these preservatives may be used as the sole preservative in the presently disclosed formulations, or they may advantageously be used in combination with each other. As shown herein, formulations of the present invention using a combination of phenoxyethanol and benzethonium chloride prove particularly preferable.

Benzethonium chloride, phenoxyethanol and phenylethyl alcohol may be used in the presently disclosed formulations in any effective amount. The total preservative concentration is preferably between about 0.001% and about 4.0% of the total formulation. Particularly advantageous concentrations of total preservative are those maintained as low as possible to achieve the requisite antimocrobial effect, while minimizing the potential for adverse reactions.

When benzethonium chloride is used as the sole preservative, it is advantageously employed in concentrations of from about 0.001 to about 1.0%. More preferably, benzethonium chloride, when used as the sole preservative, may be employed in concentrations ranging from about 0.01 to about 0.5%, or 0.02 to about 0.8%, and most preferably in a concentration of from about 0.01 to 0.02% of the total composition.

When phenoxyethanol is used in the absence of other preservatives such as benzethonium chloride, the EPO formulation will meet United States regulatory requirements when the phenoxyethanol content is 0.5%. Preferable concentrations of phenoxyethanol range from about 0.1 to about 3.0%, and more preferably from about 0.25 to about 2.0%. Most preferable concentrations of phenoxyethanol, when used as the sole preservative, range from about 0.5% to about 1.0%. When phenylethyl alcohol is used as the sole preservative, preferred concentrations are from about 0.01 to about 2.0%. Preferred concentrations range from about 0.1 to about 1.0%, with most preferred concentrations ranging from about 0.25 to about 0.5%.

In more preferred embodiments of the present invention, both benzethonium chloride and phenoxyethanol are used together. Surprisingly, when used together these preservatives have a synergystic effect on one another, and may both be used in concentrations lower than would be required if used alone. Preferred formulations include benzethonium chloride in concentrations of from about 0.001 to about 0.1% in combination with phenoxyethanol in concentrations of from about 0.01 to about 1.0%. More preferred formulations contain benzethonium chloride in a concentration of from about 0.01% to about 0.02% and phenoxyethanol in a concentration of from about 0.25% to about 0.5%.

In another embodiment, the present invention includes benzethonium chloride in combination with phenylethyl alcohol. Preferred formulations include benzethonium chloride in concentrations of from about 0.001 to about 0.1% together with phenylethyl alcohol in concentrations of from about 0.01 to about 1.0%. More preferred formulations contain benzethonium chloride in a concentration of from about 0.15 to about 0.25% and phenylethyl alcohol in a concentration of from about 0.2 to about 0.5%. A most preferred formulation in which benzethonium chloride and phenylethyl alcohol are used in concert, includes benzethonium chloride in a concentration of about 0.02% and phenylethyl alcohol in a concentration of about 0.25%.

B. Erythropoietin

The nucleic acid sequence, amino acid sequence, three-dimensional structure, and typical glycosylation patterns of EPO are known in the art. Isolated and purified EPO from various sources is also known. Accordingly, one of skill in the art can obtain EPO for use according to the present invention by isolating and purifying the EPO from human tissue or fluids, through traditional recombinant techniques, and through gene activation processes. All of these methods are specifically contemplated to be within the scope of this patent. Additionally, any other EPO, obtained from any source, is contemplated for use according to the present invention.

C. Other Active Components

The optimal formulation according to the present invention may vary according to factors such as amount of time the formulation will be stored, conditions under which it will be stored and used, the particular patient population to which it may be administered, etc. Adjustments to the formulation by adjusting constituents of the formulations and their relative concentrations, other than the preservatives benzethonium chloride, phenoxyethanol and phenylethyl alcohol and EPO as described supra, may be made as needed according to the needs of the formulator, administrator or patient. Additional constituent elements of the multi-dose EPO formulations of the present invention may include water, a buffer, a surfactant or antiadsorbant, a wetting agent, and an osmolality adjusting agent. Formulation characteristics that may be modified include, for example, the pH and the osmolality, to achieve a formulation that has a pH and osmolality similar to that of human blood or tissues.

Buffers are useful in the present invention for, among other purposes, manipulation of the total pH of the pharmaceutical formulation. A variety of buffers known in the art may be used in the present formulations, such as various salts of organic or inorganic acids, bases, or amino acids, and including various forms of citrate, phosphate, tartrate, succinate, adipate, maleate, lactate, acetate, bicarbonate, or carbonate ions. Particularly advantageous buffers for use in the present invention include sodium or potassium buffers, particularly sodium phosphate. In a preferred embodiment, sodium phosphate is employed in a concentration approximating 20 mM. A particularly effective sodium phosphate buffering system comprises sodium phosphate monobasic monohydrate and sodium phosphate dibasic heptahydrate. When this combination of monobasic and dibasic sodium phosphate is used, advantageous concentrations of each are about 0.5 to about 1.5 mg/ml monobasic and about 2.0 to about 4.0 mg/ml dibasic, with preferred concentrations of about 0.9 mg/ml monobasic and about 3.4 mg/ml dibasic phosphate. The pH of the formulation changes according to the amount of buffer used. It is preferred to achieve a pH level of between 5.0 and 8.0, more preferable to have a pH of about 6.0 to about 7.5, and most preferable to develop a formulation with a pH of about 7.0.

It may also be advantageous to employ surfactants in the presently disclosed formulations. Surfactants or anti-adsorbants that prove useful according to the present invention include polyoxyethylenesorbitans, polyoxyethylenesorbitan monolaurate, polysorbate-20, such as Tween-20™, polysorbate-80, hydroxycellulose, and genapol. In a preferred embodiment, polysorbate-20 is used. When any surfactant is employed in the present invention, it is advantageous to use it in a concentration of about 0.01 to abut 0.5 mg/ml. In a particularly useful embodiment, polysorbate-20 is used in a concentration of about 0.1 mg/ml.

Additional useful additives are readily determined by those of skill in the art, according to particular needs or intended uses of the disclosed multi-dose EPO formulations. One such particularly useful additional substance is sodium chloride, which is useful for adjusting the osmolality of the formulations to achieve the desired resulting osmolality. Particularly preferred osmolalities are in the range of about 270 to about 330 mOsm/kg. The optimal osmolality of the presently disclosed formulations is approximately 300 mOsm/kg. Sodium chloride in concentrations of about 6.5 to about 7.5 mg/ml are affective for achieving this osmolality, with a sodium chloride concentration of about 7.0 mg/ml being particularly effective. Or the amount of sodium chloride can be added or adjusted to achieve an osmolality of about 270 to about 330 mOsm/kg, and preferably 300 mOsm/kg. Other useful osmolality adjusting agents include mannitol and sorbitol.

D. Preparation of the Compositions

The EPO formulations described herein may be prepared in water suitably mixed with a surfactant, such as hydroxypropylcellulose or polyoxyethylenesorbitans. In many cases, it will be preferable to include isotonic agents, for example, sugars or sodium chloride as described above. Prolonged absorption of the injectable compositions can be brought about by the use in the compositions of agents delaying absorption, for example, aluminum monostearate or gelatin. Other agents that may be employed include, but are not limited to lecithin, urea, ethylene oxide, propylene oxide, hydroxypropylcellulose, methylcellulose, or polyethylene glycol.

Aqueous compositions (inocula) as described herein may include an effective amount of EPO dissolved or dispersed in a pharmaceutically acceptable aqueous medium. Such compositions are also referred to as inocula. The use of pharmaceutically acceptable carrier media and agents for pharmaceutically active substances is well known in the art. Except insofar as any conventional media or agent is incompatible with the active ingredient, its use in the therapeutic compositions is contemplated. Supplementary active ingredients also can be incorporated into the compositions as described above.

A proteoglycan such as EPO may be formulated into a composition in a neutral or salt form. Pharmaceutically acceptable salts include the acid addition salts (formed with the free amino groups of the protein) and those that are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The therapeutic compositions of the present invention are advantageously administered in the form of injectable compositions either as liquid solutions or suspensions; solid forms suitable for solution in, or suspension in, liquid prior to injection may also be prepared. A typical composition for such purposes comprises a pharmaceutically acceptable carrier. For instance, the composition may contain 10 mg, 25 mg, 50 mg or up to about 100 mg of human serum albumin per milliliter of phosphate buffered saline The formulations as described herein may be contained in a vial, bottle, tube, syringe or other container for single or multiple administrations. Such containers may be made of glass or a polymer material such as polypropylene, polyethylene, or polyvinylchloride, for example. Preferred containers may include a seal, or other closure system, such as a rubber stopper that may be penetrated by a needle in order to withdraw a single dose and then re-seal upon removal of the needle. All such containers for injectable liquids, lyophilized formulations, reconstituted lyophilized formulations or reconstitutable powders for injection known in the art are contemplated for use in the present disclosed compositions and methods.

EXAMPLES

The following examples are illustrative only and are not to be construed as intended to limit the scope of the invention.

A. Example 1

Preservative Selection and Stability Testing

Materials and Methods:

Sodium phosphate monobasic monohydrate USP, sodium phosphate dibasic heptahydrate USP, sodium chloride USP/EP, and polysorbate 20 USP/NF were obtained from J.T. Baker, a division of Mallinckrodt Baker, Inc., Phillipsburg, N.H. 08865.

Benzalkonium chloride USP/NF, 2-phenoxyethanol BP, phenylethyl alcohol USP/NF, thimerosal USP/NF, phenol crystals USP, benzethonium chloride USP/NF, m-cresol USP, phenyl mercuric nitrate USP/NF, benzyl alcohol USP, chlorobutanol USP, methylparaben USP/NF, and propylparaben USP/NF were obtained from Spectrum Quality products INC., Gardena, Calif. 90248.

Myristyl gamma-picolinium chloride was obtained from Pharmacia & Upjohn Company, Kalamazoo, Mich. 49001.

Multi-dose EPO-containing solutions were formulated as sterile, non-pyrogenic, colorless aqueous solutions in water for injection at 10,000 units and 20,000 units concentration. Solutions prepared contained a 20 mM phosphate buffer (sodium phosphate monobasic monohydrate, and sodium phosphate dibasic heptahydrate), 0.01% w/v polysorbate 20 as an antiadsorbent, 0.45-0.8% w/v sodium chloride (depending on the preservative system that was used, the amount of sodium chloride was adjusted to produce an Osmolality of approximately 300 mOsm/kg), and a preservative system. Solutions prepared had a pH of approximately 7.0, and an Osmolality of approximately 300 mOsm/kg.

Solutions were sterilized by filtration through a sterile 0.22-micron Millipore filter. Solutions were packaged in sterile, clear 2 ml USP type 1 glass vials and stored at 5° C. and 25° C. for chemical stability testing and in sterile 250-500 ml HDPP (high density polypropylene) bottles for microbial testing.

Preservatives studied included: benzyl alcohol 1.0% w/v, benzalkonium chloride 0.01% w/v, 2-phenoxyethanol 0.5% w/v, phenylethyl alcohol 0.5% w/v, thimerosal 0.005% and 0.01% w/v, phenol crystals 0.4% w/v, benzethonium chloride 0.01% and 0.02% w/v, m-cresol 0.4% w/v, phenyl mercuric nitrate 0.002% w/v, methylparaben 0.1 and 0.18% w/v, and propylparaben 0.03% and 0.035% w/v, and myristyl-gamma-picolinium chloride 0.02% w/v. Also, the following combinations were studied: (1) benzethonium chloride 0.005% w/v with phenoxyethanol 0.25% w/v; (2) benzethonium chloride 0.005% and phenoxyethanol 0.5% w/v; (3) benzethonium chloride 0.01% w/v with phenoxyethanol 0.5% w/v; and (4) phenylethyl alcohol 0.25% w/v and benzethonium chloride 0.02% w/v.

Discussion:

Methyl paraben, propyl paraben, m-cresol, and phenol produced hazy to cloudy solutions when added to the EPO formulation (buffered solution). This cloudiness problem was identified as an incompatibility between the absorbent polysorbate 20, and each of these preservatives (Handbook of Pharmaceutical Excipients, 1994).

Although chlorobutanol produced a clear solution when used in the formulation, its evaluation was stopped because it is not stable at pH>3, its half-life at pH 7.5 is approximately 3 months (Handbook of Pharmaceutical Excipients, 1994).

In the presence of phenyl mercuric nitrate, a cloudy solution was produced. This cloudiness was identified as an incompatibility between the osmotic agent sodium chloride, and phenyl mercuric nitrate (Handbook of Pharmaceutical Excipients, 1994).

Thimerosal produced a clear solution when used in the EPO formulation. Also, it showed good preservative efficacy. Additionally, the EPO formulation showed good chemical stability in the presence of thimerosal. However, since it contains mercury, its use is likely to be unacceptable by the agencies in Europe, Japan and US.

Formulations containing benzyl alcohol, benzethonium chloride, phenoxyethanol, phenylethyl alcohol, benzalkonium chloride, and myristyl-gamma-picolinium chloride produced clear solutions. Based on the minimum inhibitory concentrations for these preservatives, safety, and frequency of their use, the following preservatives were selected for further chemical evaluation of the protein stability and anti-microbial effectiveness of the EPO formulation: benzyl alcohol, benzethonium chloride, phenoxyethanol, phenylethyl alcohol, and several benzethonium chloride & phenoxyethanol combinations.

B. Example 2

Stability of Protein Tested

Materials and Methods:

Prototype batches were made using these selected preservatives and placed on stability at 5° C. and 25° C. Samples were tested by a reverse phase HPLC method. The assay results (% label claim) of the EPO containing formulations in the presence of these preservatives are shown in Table 2.

Label claim was determined by reverse phase HPLC using a Waters Delta-Pak™ C18 column and gradient elution using an aqueous solution containing 0.05% TFA and acetonitrile concentration which increases from 23 to 86%. Detection of the EPO protein was monitored at 210 nm.

TABLE 2

ASSAY RESULTS IN TERMS OF CONCENTRATION (% LABEL CLAIM)

| Preservative | Months | Strength | Chemical Assay (% LC)[1] | |
|---|---|---|---|---|
| | | | 5° C. | 25° C. |
| Benzyl Alcohol | 7 M | 10,000 U/ml | 98.6 | 90.0 |
| Benzyl Alcohol | 7 M | 20,000 U/ml | 99.7 | 93.7 |
| Benzethonium | 4 M | 10,000 U/ml | 99.9 | 88.9 |
| Benzethonium | 4 M | 20,000 U/ml | 101.5 | 94.4 |
| Phenoxyethanol | 4 M | 10,000 U/ml | 100.5 | 96.9 |
| Phenoxyethanol | 4 M | 20,000 U/ml | 102.6 | 97.5 |
| Benzethonium & Phenoxyethanol (0.005% & 0.5%) | 3 M | 20,000 U/ml | 98.3 | 97.0 |

[1]as measured by reverse phase HPLC.

As can be seen from table 2, the reverse-phase HPLC data show no loss of concentration of EPO for all formulas when stored at 5° C. for up to 3-7 months. However, formulas containing benzyl alcohol or benzethonium chloride alone showed up to 10% loss of EPO when stored at 25° C. for up to 3-7 months. Formulas containing phenoxyethanol or phenoxyethanol & benzethonium chloride in combination showed no loss of EPO when stored at 25° C. for up to 3-4 months. These results show the stabilizing effect of phenoxyethanol and phenoxyethanol & benzethonium chloride in combination on EPO, this effect is surprising and unexpected as well as extremely advantageous.

C. Example 3

Preservative Challenge Test

Preservative effectiveness tests are Compendial-guided assays that determine efficacy for preservative systems in multi-dose pharmaceutical preparations. In such assays, test formulations are challenged with standardized suspensions of indicator aerobic bacteria and molds and microorganism survival is monitored over a 28-day period.

Table 3 shows the results of the United States Pharmacopia (USP) and European Pharmacopia (EP) preservative challenge testing. All tested formulas passed the USP criteria for preservative challenge test. Formulas containing 0.01% w/v benzethonium chloride, 0.5% w/v phenoxyethanol, or 0.5% w/v phenylethyl alcohol failed the EP criteria for preservative challenge test. Formulas containing benzethonium chloride and phenoxyethanol in different combinations and benzethonium chloride and phenylethyl alcohol in combination passed both the USP and the EP criteria. Based on the data shown in table 3, it appears that the antimicrobial activity of benzethonium chloride was surprisingly increased by the addition of phenoxyethanol, in a synergistic manner.

TABLE 3

PRESERVATIVE CHALLENGE TESTING

| Preservative | Strength | Preservative Challenge USP | Preservative Challenge EP |
|---|---|---|---|
| Benzyl Alcohol (1.0%) | 20,000 U/ml | passed | not done |
| Benzethonium (0.01%) | 20,000 U/ml | passed | failed |
| (0.02%) | | passed | passed |
| Phenoxyethanol (0.5%) | 20,000 U/ml | passed | failed |
| Benzethonium & Phenoxyethanol (0.005 & 0.25%) (0.005 & 0.5%) (0.01 & 0.5%) | 20,000 U/ml | passed | passed |
| Phenylethyl Alco. 0.5% | 20,000 U/ml | passed | failed |
| Benzethonium & Phenylethyl Alco (0.02% & 0.25%) | 20,000 U/ml | passed | passed |

REFERENCES

U.S. Pat. No. 4,377,573 to Sugimoto et al.
U.S. Pat. No. 4,703,008 to Lin.
U.S. Pat. No. 4,806,524 to Kawagachi et al.
U.S. Pat. No. 5,503,827 to Woog et al.
U.S. Pat. No. 5,661,125 to Stricklan et al.
Handbook of Pharmaceutical Excipients, second edition, 1994.
L. A. Trissel, "Handbook on Injectible Drugs." Ed. 8, American Society of Hospital Pharmacists, Inc. 1994.
Miyaka et al., "Purification of Human Erythropoietin," *J. Biol. Chem.*, 252(15):5558-5564, 1997
Physicians' Desk Reference, ed. 48, 1994.
Physicians' Desk Reference, ed. 50, 1996.
Sandeep Nema, R. J. Washkuhn, and R. J. Brendel, "Excipients and Their Use in Injectable Products," *PDA Journal of Pharmaceutical Sciences & Technology*, Vol. 51(4), July-August 1997.
Shewood et al., "Erythropoietin Production by Human Renal Carcinoma Cells in Culture." *Endocrinology*, Vol. 99(2): 504-510, 1976.
Sherwood et al., "Establishment of a Human Erythropoietin-Producing Renal Carcinoma Cell Line." *Clinical Research*, 31:323A, 1983.

The invention claimed is:

1. A pharmaceutical composition comprising a stable, sterile, multi-dose formulation of erythropoietin; and 0.001 to 0.01% w/v benzethonium chloride; and at least one of 0.01 to 0.5% w/v phenoxyethanol or 0.01 to 0.5% w/v phenylethyl alcohol.

2. The composition of claim 1, wherein the composition comprises phenoxyethanol in a concentration of 0.01 to 0.5% w/v.

3. The composition of claim 2, further defined as comprising benzethonium chloride in a concentration of 0.005% w/v, and phenoxyethanol in a concentration of 0.25% w/v.

4. The composition of claim 2, further defined as comprising benzethonium chloride in a concentration of 0.005% w/v, and phenoxyethanol in a concentration of 0.5% w/v.

5. The composition of claim 2, further defined as comprising benzethonium chloride in a concentration of 0.01% w/v and phenoxyethanol in a concentration of 0.5% w/v.

6. The composition of claim 1, wherein the composition comprises phenylethyl alcohol in a concentration of 0.01 to 0.5% w/v.

7. The composition of claim 6, further defined as comprising benzethonium chloride in a concentration of 0.01% w/v, and phenylethyl alcohol in a concentration of 0.25% w/v.

8. The composition of claim 1, wherein the concentration of benzethonium chloride is 0.005% w/v.

9. The composition of claim 1, wherein the concentration of benzethonium chloride is 0.01% w/v.

10. The composition of claim 1, further defined as comprising a salt.

11. The composition of claim 10, wherein said salt is sodium chloride.

12. The composition of claim 1, further defined as comprising a buffer.

13. The composition of claim 12, wherein said buffer is sodium phosphate.

14. A vial for containing multiple dosages of erythropoietin, wherein said vial contains a solution comprising erythropoietin; 0.001 to 0.01% w/v benzethonium chloride; and at least one of 0.01 to 0.5% w/v phenoxyethanol or 0.01 to 0.5% w/v phenylethyl alcohol.

15. The vial of claim 14, wherein said solution comprises phenoxyethanol in a concentration of 0.01 to 0.5% w/v.

16. The vial of claim 15, further defined as comprising benzethonium chloride in a concentration of 0.005% w/v, and phenoxyethanol in a concentration of 0.25% w/v.

17. The vial of claim 15, further defined as comprising benzethonium chloride in a concentration of 0.005% w/v, and phenoxyethanol in a concentration of 0.5% w/v.

18. The vial of claim 15, further defined as comprising benzethonium chloride in a concentration of 0.01% w/v, and phenoxyethanol in a concentration of 0.5% w/v.

19. The vial of claim 14, wherein said solution comprises phenylethyl alcohol in a concentration of 0.01 to 0.5% w/v.

20. The vial of claim 19, further defined as comprising benzethonium chloride in a concentration of 0.01% w/v, and phenylethyl alcohol in a concentration of 0.25% w/v.

21. The vial of claim 14, wherein the concentration of benzethonium chloride is 0.005% w/v.

22. The vial of claim 14, wherein the concentration of benzethonium chloride is 0.01% w/v.

23. The vial of claim 14, wherein said solution further comprises a salt.

24. The vial of claim 23, wherein said salt is sodium chloride.

25. The vial of claim 14, wherein said solution further comprises a buffer.

26. The vial of claim 25, wherein said buffer is sodium phosphate.

27. A method of inhibiting microbial growth in a solution comprising erythropoietin, said method comprising adding to said solution: benzethonium chloride to a concentration of 0.001 to 0.01% w/v; and at least one of phenoxyethanol to a concentration of 0.01 to 0.5% w/v or phenylethyl alcohol to a concentration of 0.01 to 0.5% w/v.

28. The method of claim 27, wherein said method comprises adding phenoxyethanol to said solution to a concentration of 0.01 to 0.5% w/v.

29. The method of claim 28, wherein benzethonium chloride is added to a concentration of 0.005% w/v, and phenoxyethanol is added to a concentration of 0.25% w/v.

30. The method of claim 28, wherein benzethonium chloride is added to a concentration of 0.005% w/v, and phenoxyethanol is added to a concentration of 0.5% w/v.

31. The method of claim 28, wherein benzethonium chloride is added to a concentration of 0.01% w/v, and phenoxyethanol is added to a concentration of 0.5% w/v.

32. The method of claim 27, wherein said method comprises adding phenylethyl alcohol to said solution to a concentration of 0.01 to 0.5% w/v.

33. The method of claim 32, wherein benzethonium chloride is added to a concentration of 0.01% w/v, and phenylethyl alcohol is added to a concentration of 0.25% w/v.

34. The method of claim 27, wherein said benzethonium chloride is added to a concentration of 0.005% w/v.

35. The method of claim 27, wherein said benzethonium chloride is added to a concentration of 0.01% w/v.

36. The method of claim 27, further comprising adding a salt to said solution.

37. The method of claim 36, wherein said salt is sodium chloride.

38. The method of claim 27, further comprising adding a buffer to said solution.

39. The method of claim 38, wherein said buffer is sodium phosphate.

* * * * *